(12) United States Patent
Sampson et al.

(10) Patent No.: US 8,595,235 B1
(45) Date of Patent: Nov. 26, 2013

(54) METHOD AND SYSTEM FOR USING OCR DATA FOR GROUPING AND CLASSIFYING DOCUMENTS

(75) Inventors: Steven Sampson, Paris (FR); Yann Prudent, Villeneuve le roi (FR)

(73) Assignee: EMC Corporation, Hopkinton, MA (US)

(*) Notice: Subject to any disclaimer, the term of this patent is extended or adjusted under 35 U.S.C. 154(b) by 0 days.

(21) Appl. No.: 13/432,139

(22) Filed: Mar. 28, 2012

(51) Int. Cl.
*G06F 7/00* (2006.01)
*G06F 17/30* (2006.01)
*G06F 19/24* (2011.01)
*G06F 19/00* (2011.01)

(52) U.S. Cl.
CPC .... *G06F 17/30705* (2013.01); *G06F 17/30722* (2013.01); *G06F 19/24* (2013.01); *G06F 19/707* (2013.01)
USPC ............................ 707/737; 707/749; 707/758

(58) Field of Classification Search
CPC .................. G06F 17/30705; G06F 17/30722; G06F 19/24; G06F 19/707
USPC .......................................... 707/737, 749, 758
See application file for complete search history.

(56) References Cited

U.S. PATENT DOCUMENTS

| | | | |
|---|---|---|---|
| 5,987,460 A * | 11/1999 | Niwa et al. | 707/999.004 |
| 8,032,551 B2 * | 10/2011 | Schneider | 707/770 |
| 8,386,264 B2 * | 2/2013 | Hori et al. | 704/275 |
| 8,452,132 B2 * | 5/2013 | Isaev et al. | 382/309 |
| 2002/0161753 A1 * | 10/2002 | Inaba et al. | 707/3 |
| 2005/0071365 A1 * | 3/2005 | Hou et al. | 707/102 |
| 2008/0065618 A1 * | 3/2008 | Maluf | 707/5 |
| 2010/0121642 A1 * | 5/2010 | Hori et al. | 704/254 |
| 2010/0287173 A1 * | 11/2010 | Schneider | 707/759 |
| 2013/0054595 A1 * | 2/2013 | Isaev et al. | 707/736 |

* cited by examiner

*Primary Examiner* — Phong Nguyen
(74) *Attorney, Agent, or Firm* — Dergosits & Noah LLP; Todd A. Noah

(57) ABSTRACT

Document classes for classifying documents are created by comparing the spatial relations of words between a first and second document. If the spatial relations are the same, a document class may be created to classify documents similar to the first and second document. If the spatial relations are different, a first document class may be created to classify documents similar to the first document, and a second document class may be created to classify documents similar to the second document.

20 Claims, 16 Drawing Sheets

705

Skyway Productions
*Making a better tomorrow today*

76 Paxson Lane, Miami, FL 90210
Phone 555-785,9863
Fax 555-735-8514

717 — INVOICE
715 — INVOICE: 78
DATE: 2/5/2012
720

TO:
Adam Smith
Light Star, Inc.
17 Ortega Ave
Westchester, PA 94755
555.662.7485

FOR:
Patriot Towers
P.O. #12

| Description | HOURS | RATE | AMOUNT |
|---|---|---|---|
| Install 45' copper line | 14 | $90.00 | $1260.00 |
| Remove extg fountain | 5 | $50 | $250.00 |
| Install underground tank | 10 | $80 | $800.00 |
| | | | |
| | | | |
| | | | |
| | | | |
| | | | |
| | | TOTAL 725 | $2310.00 |

Total due in 15 days. Overdue accounts subject to a service charge of 1% per month.

Figure 7

Skyway Productions     805     817 —— INVOICE

*Making a better tomorrow today*

356 Casale Place, Dublin, FL 19042
Phone 555-943-8822
Fax 555-943-8311

815 —— INVOICE #92
DATE: 3/8/2012
820 ——

TO:
Paul Brodie
Ibis Tech, Inc.
55 Paradise Ave
Castro, NY 19115
555-585-5115

FOR:
Shuttle
P.O. #88

| DESCRIPTION | HOURS | RATE | AMOUNT |
| --- | --- | --- | --- |
| Install return air duct | 10 | $100.00 | $1000.00 |
| Paint exterior | 5 | $50 | $250.00 |
| Adjust flow pressure | 1 | $80 | $80.00 |
|  |  |  |  |
|  |  |  |  |
|  |  |  |  |
|  |  |  |  |
|  |  |  |  |
|  |  |  |  |
|  |  |  |  |
|  |  |  |  |
|  |  |  |  |
|  |  | TOTAL | $1330.00 |

825 ——

Total due in 15 days. Overdue accounts subject to a service charge of 1% per month.

```
Generate a set of word pairs, each pair including a word from a first
document and a corresponding word from a second document
1115
                            ↓
Compute first location information for a word of a word pair that
indicates a location of the word relative to other words in the first
document
1120
                            ↓
Compute second location information for a corresponding word of
the word pair that indicates a location of the corresponding word
relative to other words in the second document
1125
                            ↓
Compare the first and second location information
1130
                            ↓
Return a score responsive to the comparison
1135
```

Figure 11

METHOD AND SYSTEM FOR USING OCR DATA FOR GROUPING AND CLASSIFYING DOCUMENTS

BACKGROUND

The present invention relates to the field of information technology, including, more particularly, to systems and techniques for document processing.

For most organizations, information can be the foundation for competitive differentiation—from faster processing time and reduced operating costs to quicker access to information and ensured compliance. Or, by sheer volume and complexity alone, it can thwart productivity, waste time and resources, and strain the IT infrastructure that supports it.

A key to utilizing information successfully is the ability to efficiently capture and manage large volumes of information from disparate sources. Business critical information arrives in many forms including paper and fax. Transforming the information into intelligent content can feed enterprise applications such as enterprise content management, enterprise resource planning, customer relationship management, and other information systems.

It can be very difficult to group and classify paper documents that have been scanned because of optical character recognition (OCR) errors, differences in text, differences in graphics, noise, stray marks, rotations, skewing, handwriting, and so forth.

Thus, there is a need to provide systems and techniques for automatically grouping and classifying documents.

BRIEF DESCRIPTION OF THE FIGURES

FIG. 7 shows a third example of a document.

FIG. 8 shows a fourth example of a document.

FIG. 11 shows a flow of a textual distance function used to compare documents.

DETAILED DESCRIPTION

Figure 1:
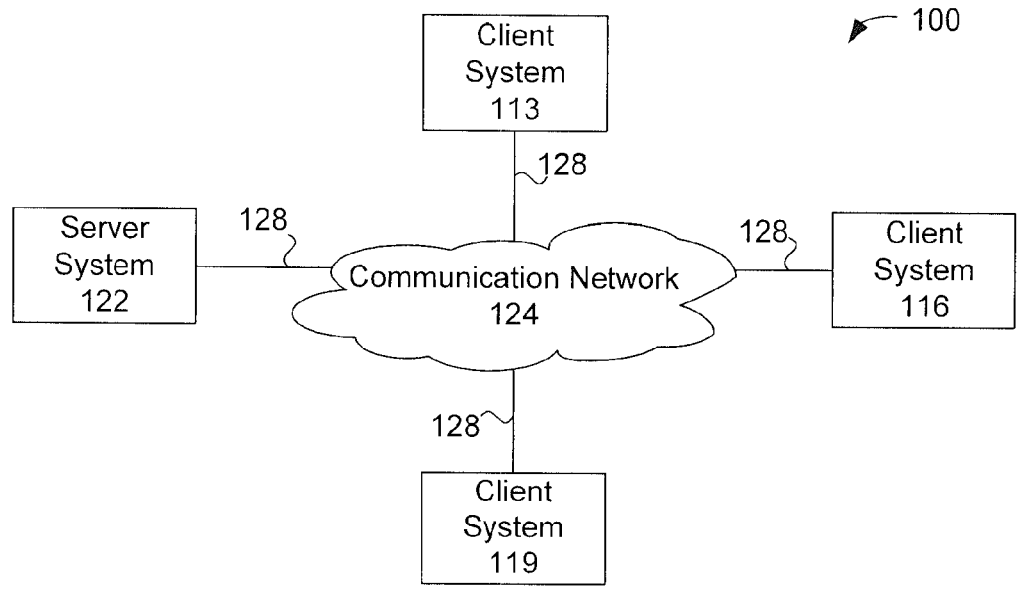
FIG. 1 shows a block diagram of a client-server system and network in which an embodiment of the invention may be implemented.

FIG. 1 is a simplified block diagram of a distributed computer network 100. Computer network 100 includes a number of client systems 113, 116, and 119, and a server system 122 coupled to a communication network 124 via a plurality of communication links 128. There may be any number of clients and servers in a system. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information. Various communication protocols may be used to facilitate communication between the various systems shown in FIG. 1. These communication protocols may include TCP/IP, HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, a intranet, a private network, a public network, a switched network, and combinations of these, and the like.

Distributed computer network 100 in FIG. 1 is merely illustrative of an embodiment and is not intended to limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server system which provides the information. For this reason, server systems typically have more computing and storage capacity than client systems. However, a particular computer system may act as both a client or a server depending on whether the computer system is requesting or providing information. Additionally, although aspects of the invention have been described using a client-server environment, it should be apparent that the invention may also be embodied in a stand-alone computer system. Aspects of the invention may be embodied using a client-server environment or a cloud-computing environment.

Server 122 is responsible for receiving information requests from client systems 113, 116, and 119, performing processing required to satisfy the requests, and for forwarding the results corresponding to the requests back to the requesting client system. The processing required to satisfy the request may be performed by server system 122 or may alternatively be delegated to other servers connected to communication network 124.

Client systems 113, 116, and 119 enable users to access and query information stored by server system 122. In a specific embodiment, a "Web browser" application executing on a client system enables users to select, access, retrieve, or query information stored by server system 122. Examples of web browsers include the Internet Explorer browser program provided by Microsoft Corporation, and the Firefox browser provided by Mozilla Foundation, and others.

Figure 2:
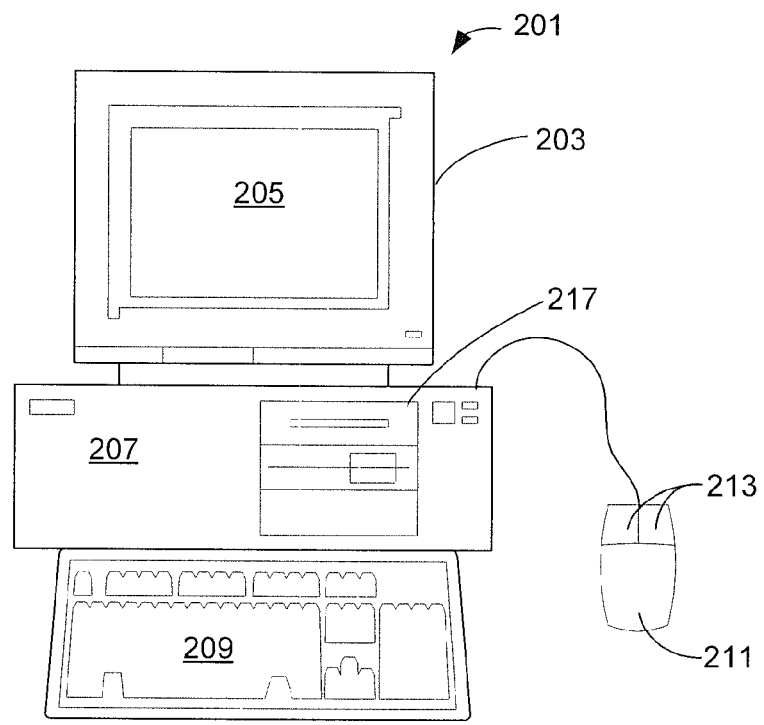
FIG. 2 shows a more detailed diagram of an exemplary client or computer which may be used in an implementation of the invention.

FIG. 2 shows an exemplary client or server system. In an embodiment, a user interfaces with the system through a computer workstation system, such as shown in FIG. 2. FIG. 2 shows a computer system 201 that includes a monitor 203, screen 205, cabinet 207, keyboard 209, and mouse 211. Mouse 211 may have one or more buttons such as mouse buttons 213. Cabinet 207 houses familiar computer components, some of which are not shown, such as a processor, memory, mass storage devices 217, and the like.

Mass storage devices 217 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

A computer-implemented or computer-executable version of the invention may be embodied using, stored on, or associated with computer-readable medium or non-transitory computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software may also be stored or reside on mass storage device 217 (e.g., hard disk, magnetic disk, tape, or CD-ROM). As a further example, code may be transmitted via wires, radio waves, or through a network such as the Internet.

Figure 3:
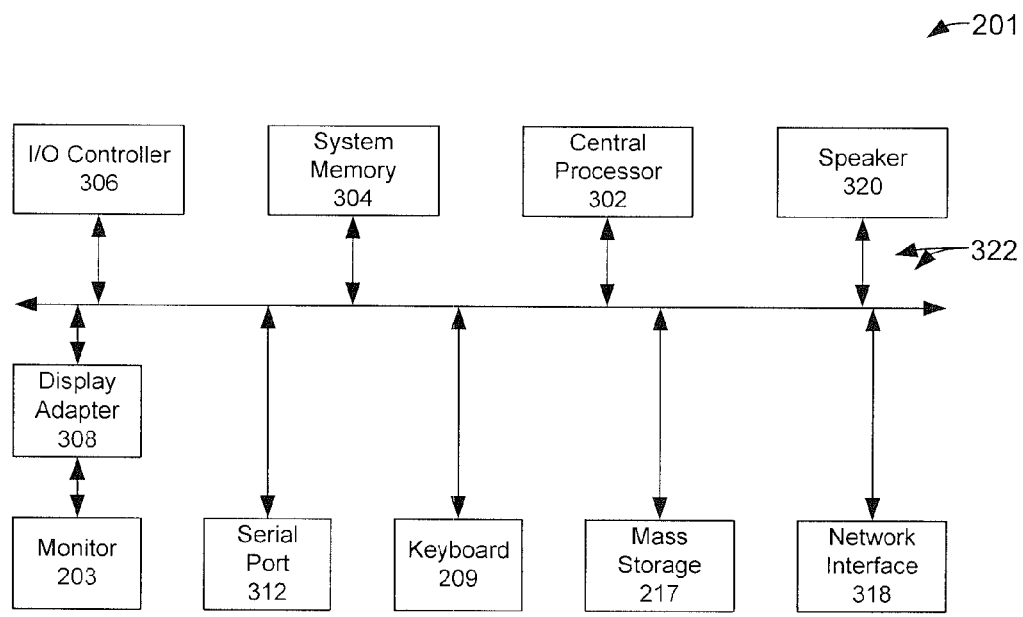
FIG. 3 shows a system block diagram of a client computer system.

FIG. 3 shows a system block diagram of computer system 201. As in FIG. 2, computer system 201 includes monitor 203, keyboard 209, and mass storage devices 217. Computer system 201 further includes subsystems such as central processor 302, system memory 304, input/output (I/O) controller 306, display adapter 308, serial or universal serial bus (USB) port 312, network interface 318, and speaker 320. In an embodiment, a computer system includes additional or fewer subsystems. For example, a computer system could include more than one processor 302 (i.e., a multiprocessor system) or a system may include a cache memory.

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. The processor may include multiple processors or a multicore processor, which may permit parallel processing of information. Computer system 201 shown in FIG. 2 is but an example of a suitable computer system. Other configurations of subsystems suitable for use will be readily apparent to one of ordinary skill in the art.

Computer software products may be written in any of various suitable programming languages, such as C, C++, C#, Pascal, Fortran, Perl, Matlab (from MathWorks), SAS, SPSS, JavaScript, AJAX, Java, SQL, and XQuery (a query language that is designed to process data from XML files or any data source that can be viewed as XML, HTML, or both). The computer software product may be an independent application with data input and data display modules. Alternatively, the computer software products may be classes that may be instantiated as distributed objects. The computer software products may also be component software such as Java Beans (from Oracle Corporation) or Enterprise Java Beans (EJB from Oracle Corporation). In a specific embodiment, the present invention provides a computer program product which stores instructions such as computer code to program a computer to perform any of the processes or techniques described.

An operating system for the system may be one of the Microsoft Windows® family of operating systems (e.g., Windows 95, 98, Me, Windows NT, Windows 2000, Windows XP, Windows XP x64 Edition, Windows Vista, Windows 7, Windows CE, Windows Mobile), Linux, HP-UX, UNIX, Sun OS, Solaris, Mac OS X, Alpha OS, AIX, IRIX32, or IRIX64. Other operating systems may be used. Microsoft Windows is a trademark of Microsoft Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of the system using a wireless network using a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
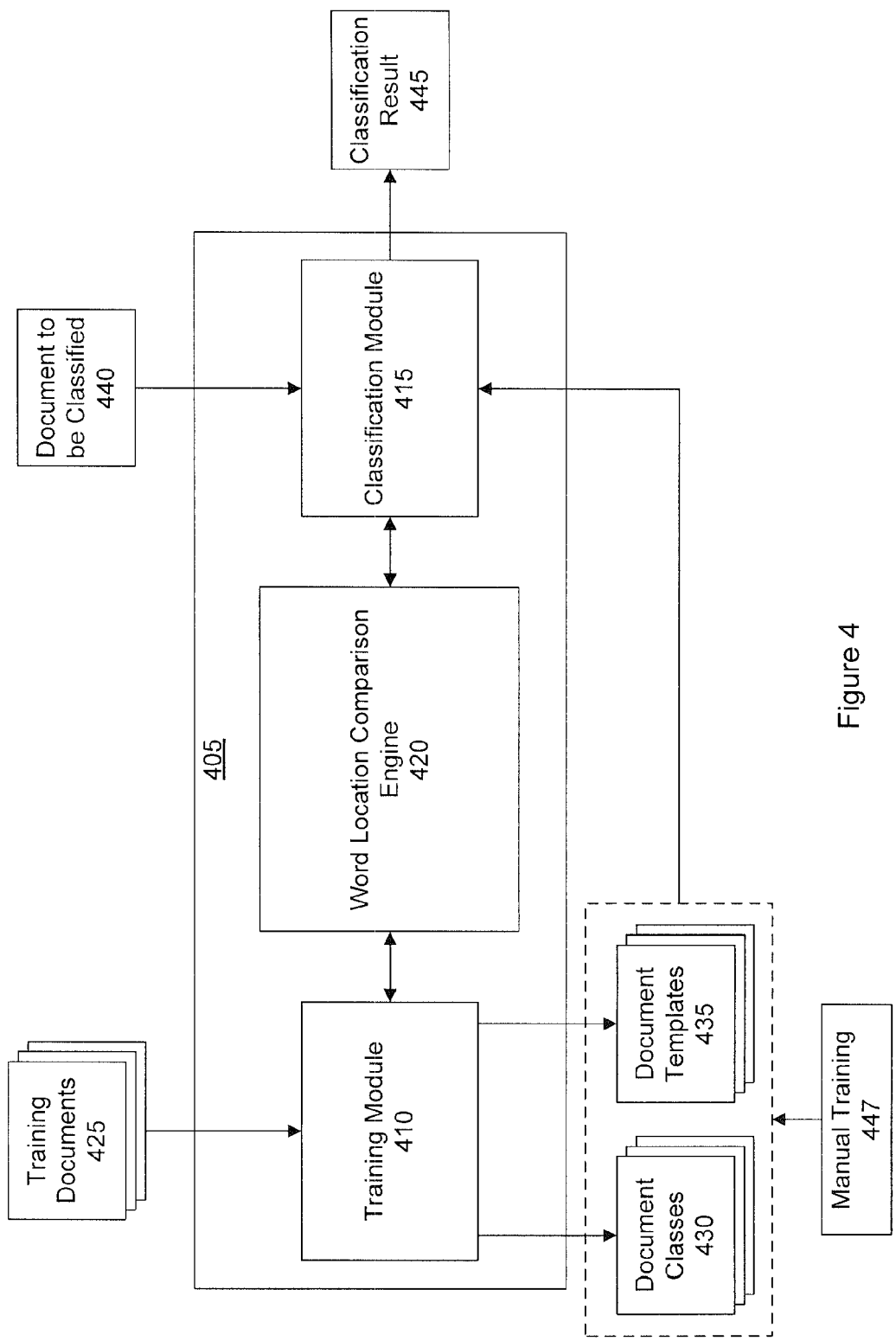
FIG. 4 shows a simplified block diagram of a specific implementation of a system for grouping and classifying documents.

FIG. 4 shows a simplified block diagram of a specific implementation of a system 405 for grouping and classifying documents. This system includes a training module 410, a classification module 415, and a location comparison engine 420 connected to the training and classification modules. In brief, the system receives as input to the training module a set of documents 425 that may be used to train the system. The training module outputs a set of document classes 430 and a set of document templates 435. Each document template is associated with a document class. The set of document classes and templates are provided to the classification module. The classification module receives as input a document 440 to be classified. The classification module outputs a classification result 445. The classification result may specify the document class in which the document should be classified.

More particularly, during a training step the location comparison engine is used to compare a document (e.g., first document) in the set of documents with another document (e.g., second document) in the set of documents. In a specific implementation, if the comparison indicates the first and second documents are similar, a document class and associated template are created for classifying documents similar to the first and second documents. If the comparison indicates the first and second documents are different, a first document class and associated first template is created for classifying documents similar to the first document. And, a second document class and associated second template is created for classifying documents similar to the second document.

In a specific implementation, the training is automated. This is not, however, always the case. In other specific implementations, the training of the system may include manual techniques. Automated training may be supplemented with manual training. For example, training may include the involvement of a user (e.g., administrator). In other words, it is possible to "train" using a human 447 (i.e., automatic learning is not the only way to create document classes/templates). A user may supervise the training and make appropriate adjustments as desired.

During a classification step, the location comparison engine can also be used to classify a document into a particular document class using the templates. For example, the location comparison engine can be used to compare the document to be classified against the document templates. Based on the comparison between the document and a document template, the document may be classified into a document class associated with the document template.

The location comparison engine uses textual content present on a page to compare two images (e.g., digitized documents or document images) to see if they belong in the same class. In an implementation, the comparison between documents uses fuzzy textual matching and spatial relations of words to determine whether two documents belong in the same class. Applicants have recognized that structured and semi-structured documents may have certain patterns that are text-based such as "Total," "Invoice #," and so forth that appear in the same relative position in each document of the same class. This application discusses techniques for learning these common text patterns and their relative locations and applying this on production document images to provide improved grouping and classification methods. This learnt information can be leveraged in extracting business data.

A specific application of the system is to capture data from scanned images including structured, semi-structured documents, or both such as invoices and forms. Classification is the process of deciding whether an object belongs in a particular class (from a set of classes). In order to classify, the system can provide a set of templates defining each object class. A training step takes a set of images and from these creates a set of classes. The images may be images of documents. That is, physical documents that have been scanned via a scanner and output as optical character recognition (OCR) data, i.e., scanned or digitized documents. The training step can be a manual process or an automated process. The classification step then compares an image with each of the classes and decides in which class or classes the image belongs. In a specific implementation, if the image belongs to only one class the image may be considered classified. Otherwise, the image may either be over-classified or not classified at all.

In an implementation, there is an automated training step, a classification step, or both which use a comparison function (which may be referred to as a distance function) to determine whether an image is "close" to another image or template. The training and classification algorithms may use this comparison function. In a specific implementation, there is a "training" comparison function that compares two images. There is a "classification" function that compares an image and a reference set of keywords.

Applicants have recognized that for structured and semi-structured documents, words sometimes consistently appear in the same place relative to each other. For example, consider that word "x" appears a distance of 20 to the right and 40 higher from a word "y" on one image. If the system finds the word "x" and "y" on the other image about 20 to the right and 40 higher apart from each other words "x" and "y" are considered to be in the same relative position—and hence increases the probability that these two documents are from the same class.

In a specific implementation, an algorithm attempts to find the set of words that appear in the same place in two documents. If only a handful of words are in common, then the documents are unlikely to be the same type of document. However, when, for example, the system finds 20-30 words all in the same place with respect to each other the system may determine that the documents are related.

Figure 5:
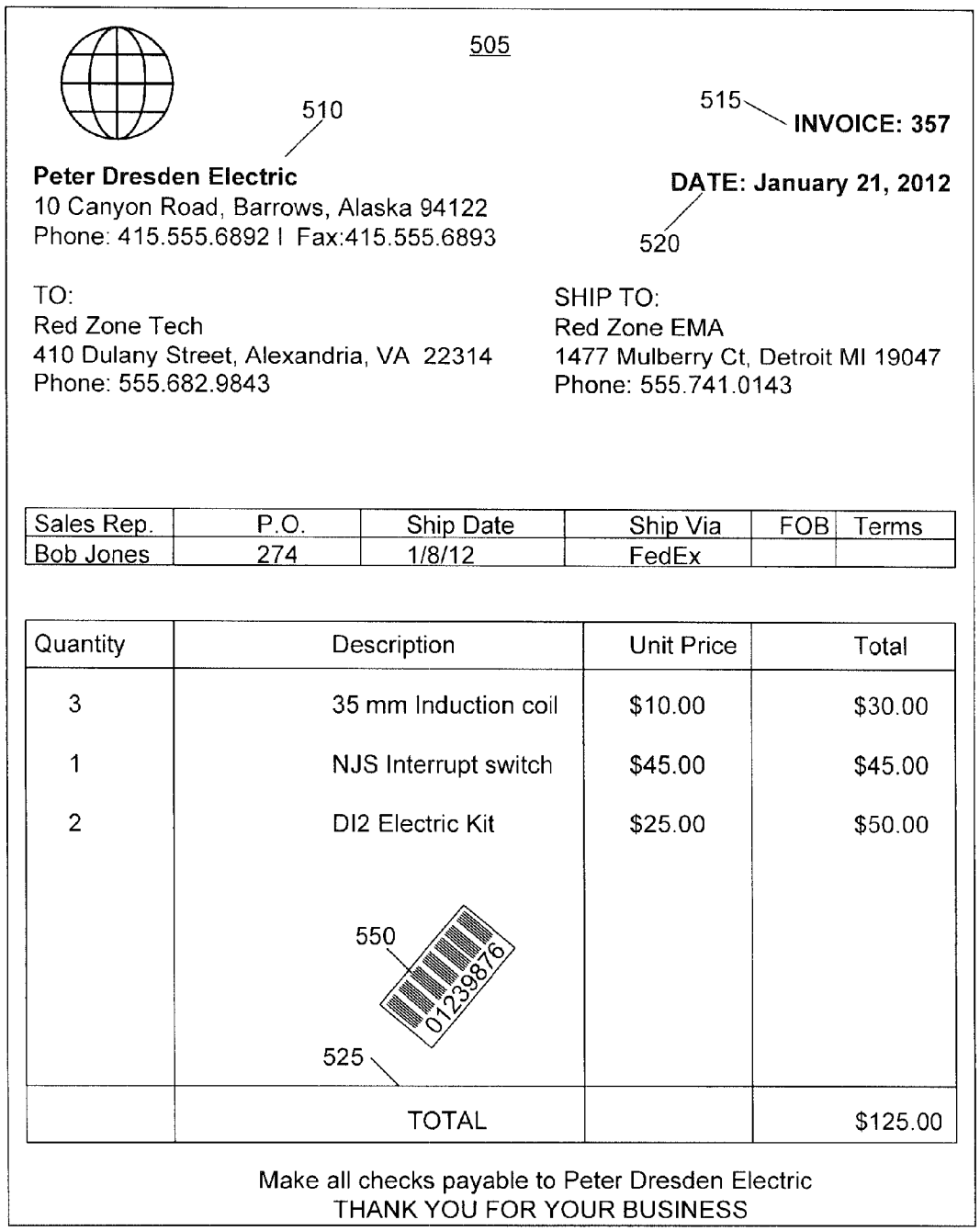
FIG. 5 shows a first example of a document.
Figure 6:
FIG. 6 shows a second example of a document.

As an example, consider FIGS. 5-7 which each show an image of a document or invoice. The two images 505 (FIG. 5) and 605 (FIG. 6) come from two documents that may be in the same class. Image 505 includes a word 510 "Dresden," a word 515 "INVOICE," a word 520 "DATE," and a word 525 "TOTAL." Image 605 includes a word 610 that corresponds to word 510 "Dresden," a word 615 that corresponds to word 515 "INVOICE," a word 620 that corresponds to word 520 "DATE," and a word 625 that corresponds to word 525 "TOTAL." These are some examples of the types of words that may be found by the algorithm. These words—"Dresden," "INVOICE," "DATE," and "TOTAL"—all appear in the same place on examples of the invoices. For example, a location of word 515 relative to word 520 on image 505 is about the same as a location of word 615 relative to word 620 on image 605.

Image 705 (FIG. 7) includes a word 715 and a word 717 that are the same as word 515 "INVOICE," a word 720 that is the same as word 520 "DATE," and a word 725 that is the same as word 525 "TOTAL." In other words, image 705 also has the words "INVOICE," "DATE," and "TOTAL." However, these words are in completely different relative positions. Because the data (such as invoice number) appears to be offset with respect to the underlying form, these data may not be found as common between the two documents. For example, a location of word 715 relative to word 720 on image 705 is different from a location of word 515 relative to word 520 on image 505.

Figure 9:
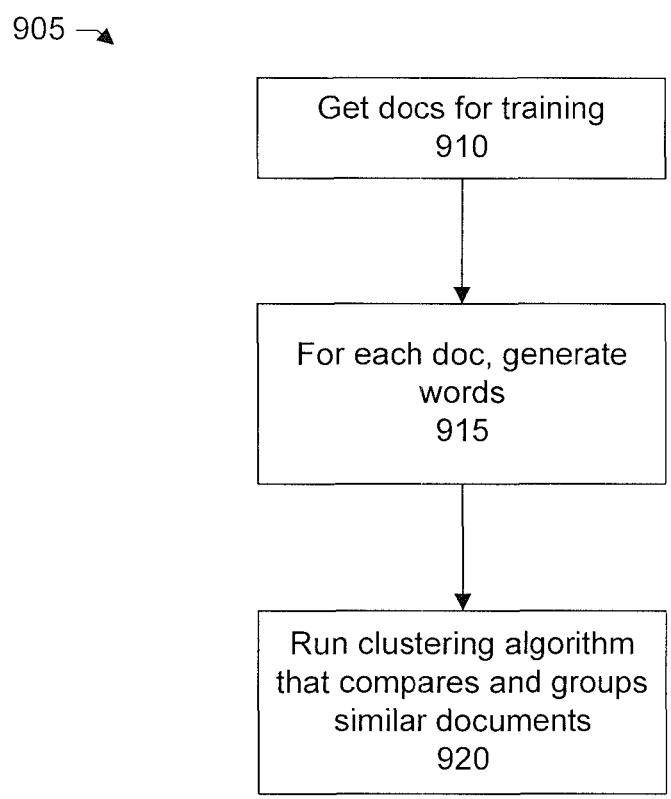
FIG. 9 shows a simplified flow for grouping and creating document classes.

FIG. 9 shows a simplified flow 905 for creating one or more classes based on a set of documents. The documents may be referred to as training documents. Some specific flows are presented in this application, but it should be understood that the process is not limited to the specific flows and steps presented. For example, a flow may have additional steps (not necessarily described in this application), different steps which replace some of the steps presented, fewer steps or a subset of the steps presented, or steps in a different order than presented, or any combination of these. Further, the steps in other implementations may not be exactly the same as the steps presented and may be modified or altered as appropriate for a particular process, application or based on the data.

In a step 910, the system receives or gets a set of documents. The documents may be received from a scanner or other device capable of providing a digital image, digitized representation, or digital representation of physical document papers. That is, the documents may be digitized documents, scanned documents, or digital representations of physical documents. Some specific examples of documents include invoices, tax forms, applications (e.g., benefit enrollment), insurance claims, purchase orders, checks, financial documents, mortgage documents, health care records (e.g., patient records), legal documents, and so forth. The documents may be from different vendors, suppliers, manufacturers, individuals, groups, companies, entities, and so forth.

In a specific implementation, the received document data includes optical character recognition (OCR) data such as a set of characters with position information, confidence information, or both. The received document data may include a set of OCR data sets, each data set being associated with a document, and including a list of characters or words.

In a step 915, for each document, the system generates a list of words. A list of words includes one or more words from the document. In a specific implementation, generating a list of words for a document includes a pretreatment process. The pretreatment process transforms the OCR data into data that is more suited to doing the comparison calculations.

In some cases, it may not be desirable to weigh certain differences between two documents to determine whether or not the documents should be in the same class. For example, in some places on forms and invoices where a number might appear, the number is likely to vary (e.g., a "Total: $123.00" and "Total: $999.99" or "Nov. 24, 2011" versus "Oct. 19, 2012"). Thus, in a specific implementation, a pretreatment technique includes altering the digits to a predefined value such as 0 to allow the system to consider different numerical values between two documents to be the "same" or be considered as the same type of data. In order to facilitate the matching of numbers, the system may change all digits to a predefined value (e.g., 0).

In this specific implementation, there is a pretreatment process for the received OCR data. A pretreatment process includes a first pretreatment sub-process to alter certain recognized characters, a second pretreatment sub-process to remove certain recognized characters, or both. In a specific implementation, the first pretreatment sub-process includes changing, altering, modifying, editing, or mapping recognized digits (e.g., 0, 1, 2, 3, 4, 5, 6, 7, 8, or 9) to a predefined value such as 0 or zero. For example, the number "123" may become "000." The pretreatment step can be equivalent to changing the fuzzy text comparison function (discussed below) to treat all numbers the same.

After altering the numerical values on the two documents to compare, the system can match "999" and "123." It should be appreciated that changing recognized digits to a predefined value is merely one example of a number matching algorithm. Other techniques including, for example, blocking, matching weights, and threshold of likelihood may instead or additionally be used.

In a specific implementation, a pretreatment process includes mapping each numerical digit of a first number in a first document to a predefined value to alter the first number to a first altered number, and mapping each numerical digit of a second number, different from the first number, in the second document to the predefined value to alter the second number to a second altered number, the same as the first altered number.

In another specific implementation, a second pretreatment sub-process includes removing words having a single character. Words having only one character may be noise from the scanning process or may be a graphic that is interpreted as a letter. In other words, 1-letter words may be removed, rejected, or flagged so that they are not considered because such words may be noise or stray marks on the page that may skew the scoring or results.

In a step 920, the system runs a clustering algorithm that compares the documents (using the generated word lists) and groups similar documents. In a specific implementation, the clustering algorithm incorporates a similarity function (which may be referred to as a distance function) which is an algorithm that makes, among other things, a set of word pairs, each word pair including a word from a first document and a word from a second document. The system takes a pair of documents and returns a "distance." The "distance" can indicate whether or not the pair of documents are similar (and thus should be in the same class) or are not similar (and thus should be in different classes).

In other words, in a specific implementation, the clustering algorithm uses the spatial relations of words to cluster and group similar documents. In this specific implementation, a function—referred to as a textual distance function—takes as input two images (e.g., digitized documents or document images) and outputs a distance or score. The distance indicates whether or not the two images are similar or not similar. In a specific implementation, the textual distance function has the form: "distance(first document, second document)."

More particularly, in a specific implementation, there is a comparison function that takes optical character recognition (OCR) data that may include a set of characters with position and confidence information from two images and finds a set of words that appear in both of the images in approximately the same relative position. Upon finding the set of common words, the set of common words is passed to a scoring function that takes into account a number and size of the common words. In this specific implementation, the score is proportional to the number of common words, the size of the common words, or both. More words and bigger words can mean a higher score as compared to fewer and smaller words. If the score exceeds a threshold value then the two images may be considered "in the same class."

Figure 10:
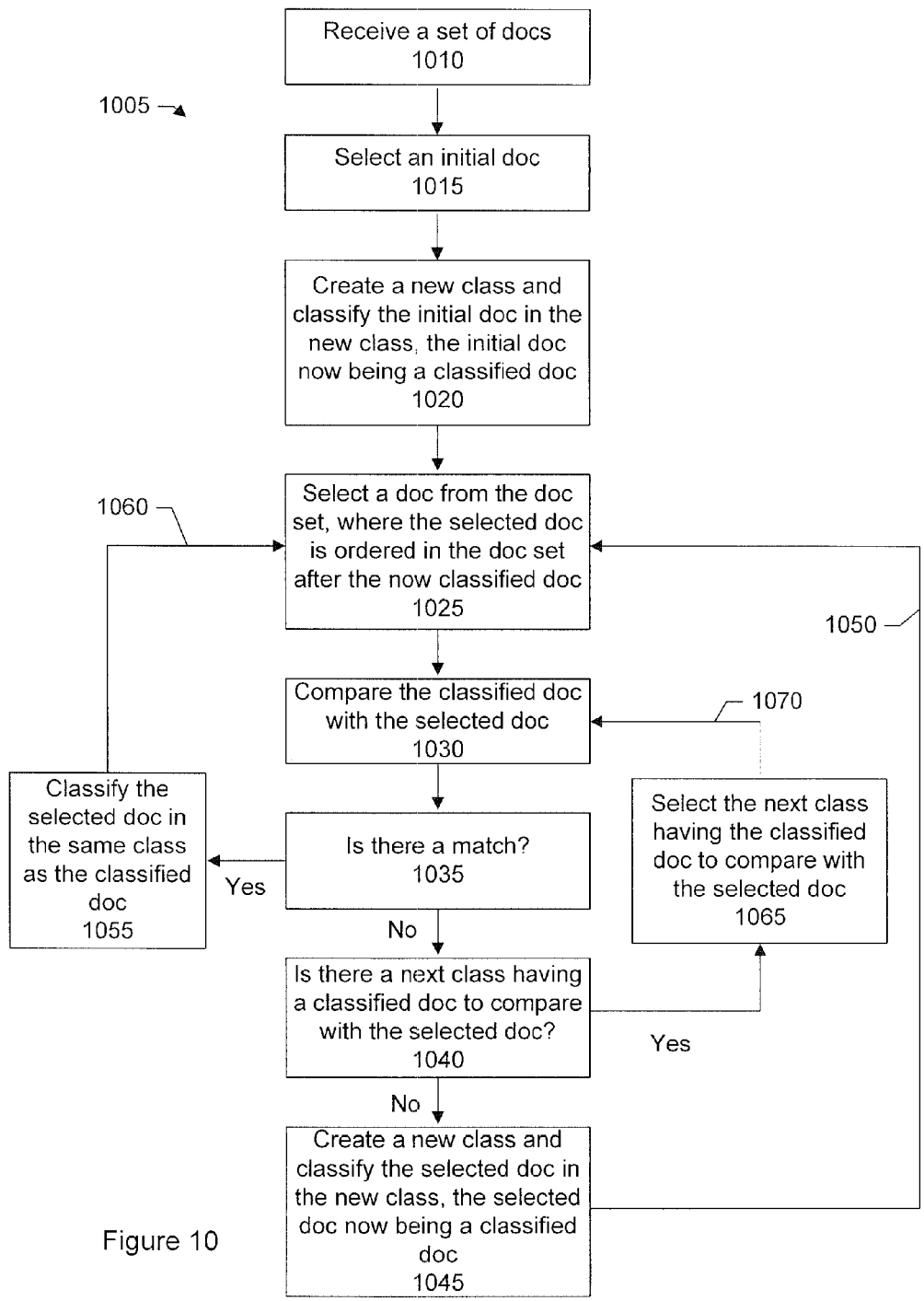
FIG. 10 shows a more detailed flow of the flow shown in FIG. 9.

FIG. 10 shows a more detailed flow 1005 of the flow shown in FIG. 9. The flow shown in FIG. 10 is used to train the system and create document classes or groups for classifying documents. In a step 1010, the system receives a set of documents for training the system, e.g., creating the document classes. In a step 1015, the system selects an initial document from the document set. In a step 1020, the system creates a new class and classifies the initial document in the new class, the initial document now being a classified document.

In a step 1025, the system selects a document from the document set. In a specific implementation, the selected document is ordered or positioned in the document set after the now classified document. In this specific implementation, the selected document is the next document in the document set immediately after the now classified document. In other implementations, the selected document may not be the document ordered immediately after the now classified document.

In a step 1030, the system compares the now classified document with the selected document. In a step 1035, the system determines whether there is a match between the classified document and the selected document.

If there is not a match, in a step 1040, the system determines whether there is another or a next class having a classified document to compare with the selected document. If there is no other class to compare, in a step 1045, the system creates a new class and classifies the selected document in the new class, the selected document now being a classified document.

After classifying the selected document, the system (assuming there are remaining documents in the document set) loops back 1050 to step 1025 to select another document that will be compared.

Referring now to step 1035, if the system determines that there is a match between the classified document and the selected document, in a step 1055, the system classifies the selected document in the same class as the classified document. After the classifying, the system (assuming there are remaining documents in the document set) loops back 1060 to step 1025 to select another document. One or more counter variables can be used to track the remaining documents, the number of classes, the number of documents in each class, and so forth.

Referring now to step 1040, if there is a next or another class having a classified document to compare with the selected document, the system in a step 1065 selects the next class having the classified document to compare with the selected document; and loops back 1070 to step 1030 to perform the comparison.

To further illustrate the flow shown in FIG. 10, consider, as an example, that we have four document types A, B, C, and D. We have specific instances of the documents A1, A2, A3, and so forth. In the document set or training set, assume we have (in this order or sequence): A1, B1, B2, A2, A3, C1, B3, C2, D1, and A4.

The clustering algorithm starts with 0 classes. It takes each image:

Document A1->does not match any existing class (no classes yet exist), create new class and add document A1. Let's call this class A. See steps 1015, 1020.

Document B1->compare with class A (distance(A1, B1)). No match. Create class B and put B1 in it. See steps 1025, 1030, 1035, 1040, and 1045.

Document B2->compare with class A (distance(A1, B2)). No match. Compare with class B (distance(B1, B2)). Match->add to class B (now has B1, B2). See steps 1025, 1030, 1040, 1065, and 1070.

Document A2->compare with class A (distance(A1, A2)). Match->add to class A (now has A1, A2). See steps 1025, 1030, 1035, and 1055.

Document A3->compare with class A (distance(A1, A3)). Match->add to class A (now has A1, A2, A3). See steps 1025, 1030, 1035, and 1055.

Document C1->compare with class A (distance(A1, C1)) and class B (distance(B1, C1). No match. Create class C and put C1 in it. See steps 1025, 1030, 1035, 1040, 1065, 1070, and 1045.

Document B3->compare with class A (distance(A1, B3)). No match. Compare with class B (distance(B1, B3). Match->add to class B (now has B1, B2, B3). See steps 1025, 1030, 1035, 1040, 1065, and 1070.

Document C2->compare with class A (distance(A1, C2)) and class B (distance(B1, C2). No match. Compare with class C. Match->add to class C (now has C1, C2). See steps 1025, 1030, 1035, 1040, 1065, and 1070.

Document D1->compare with class A (distance(A1, D0), class B (distance(B1, D1) and class C (distance(C1, D1). No match. Create class D and put D1 in it. See steps 1025, 1030, 1035, 1040, 1065, 1070, and 1045.

Document A4->compare with class A (distance(A1, A4)). Match->add to class A (now has A1, A2, A3, A4). See steps 1025, 1030, 1035, and 1055.

So at the end of this, we have 4 classes:
class A (A1, A2, A3, A4)
class B (B1, B2, B3)
class C (C1, C2)
class D (D1)

In other words, in a specific implementation, with the set of training images, a clustering algorithm is run using the textual distance. As discussed, the textual distance is a function that takes as input two images. In this specific embodiment, the algorithm includes the following procedure:

```
clusters = empty list of clusters
For each image
    is there a cluster in clusters that matches (textual score > threshold)?
        If so, add image to this cluster
        If not, create new cluster with single image and add to clusters
```

In a specific implementation, the score is increasing rather than decreasing when two documents are close. Alternatively, in another implementation, the score or code may be configured so that the score is decreasing rather than increasing when two documents are close. The system then filters for clusters that are too small (e.g., contain only a few images). This can be a customer-settable or user-configurable parameter.

Below is a sample of code for a clustering algorithm using textual distance.

```
ICollection<TCluster> Cluster(IEnumerable<TItem> items)
{
    List<TCluster> result = new List<TCluster>( );
    foreach (TItem item in items)
    {
        bool wasAdded = false;
        for (int j = 0; j < result.Count; j++)
        {
            if (TextualScore(item, result[j].item[0]) > Threshold)
            {
                result[j].Add(item);
                wasAdded = true;
                break;
            }
        }
        if (!wasAdded)
        {
            TCluster cluster = new TCluster( );
            cluster.Add(item);
            result.Add(cluster);
        }
    }
    return result;
}
```

Again, in this specific implementation, the score is increasing rather than decreasing when two documents are close. As discussed above, however, in another implementation, the score or code may be configured so that the score is decreasing rather than increasing when two documents are close.

The above clustering algorithm is merely one example of a clustering algorithm incorporating the textual distance feature as discussed in this patent application. In other implementations, the textual distance function may be incorporated into other clustering algorithms.

FIG. 11 shows a flow 1105 of a specific implementation of the textual distance function that is used to compare two documents. In a step 1115, the system generates a set of word pairs. Each word pair includes a word from a first document of the set of documents and a corresponding word from a second document of the set of documents. In a specific implementation, there is a first list of recognized words, and a second list of recognized words. The first list of recognized words includes words from a first document. The second list of recognized words includes words from a second document. The system can then take the two lists of words and create a list of the words from the one page or document that have approximately the same text and approximately the same size as the words on the other page or document. This results in a list of pairs of words (one word from each page or document). A word can include any character, symbol, number, or any combination of characters, symbols, or numbers.

Identifying the words for a word pair may be based on any number of factors. In a specific implementation, there is a first factor, a second factor, or both. The first factor is based on calculating a value of a string metric between a first word from a first document and a second word from a second document. If the value is, for example, below a threshold value the first word may be included as a word in a word pair and the second word may be included as a corresponding word in the word pair.

A string metric measures an amount of difference between two words. In a specific implementation, the string metric is a "Levenshtein distance" which is a means of getting a distance between two strings. That is, a Levenshtein distance is used to determine whether a first word from a first document and a second word from a second document should be in a word pair, the first word being a word in the word pair and the second word being a corresponding word in the word pair.

It should be appreciated that other approximate string matching algorithms, fuzzy string searching, or edit distance metrics may instead or additionally be used, e.g., length of the longest common subsequence, a Damerau-Levenshtein distance, or a Hamming distance. These string matching techniques can be used to compensate for mistakes that may be made by an OCR engine. For example, OCR engines may confuse "I" and "l" (upper case "I" and lower case "L," respectively) and "rn" with "m." To compensate for such errors, the system can use a fuzzy definition of "same."

The second factor is based on calculating a size or area of the words. If an area occupied by a first word on a first document is about the same as an area occupied by a second word on a second document, the first word may be included as a word in a word pair and the second word may be included as a corresponding word in the word pair. Generally, it is undesirable to match two words of different sizes or consider them to be "same" or corresponding to each other. In other words, it is desirable to match words having approximately the same size (e.g., font size).

For example, the word "Invoice" may be the first and second words on a first and second document, respectively. On the first document, the word may be in a 12-point font size. On the second document, however, the word may be in a 48-point font size. The difference in size may indicate that the two words should not be considered as a pair. Thus, even though the text of the first and second words is the same, the system may determine that the first and second words are not corresponding to be included in a word pair because of the difference in the size of the words.

For example, FIGS. 7 and 8 show two variants of a layout. A document 805 (FIG. 8) has the same layout as document 705 (FIG. 7) with different content. The word "Invoice" on FIG. 7 appears two times (see word 715 and word 717 that is above word 715). With these two words in two documents containing words 715 and 717, there can be four combinations or four possible word pairs. A word pair will include one word from each document. A first combination includes INVOICE (717), INVOICE (817). A second combination includes INVOICE (715), INVOICE (815). A third combination includes INVOICE (717), INVOICE (815). A fourth combination includes INVOICE (715), INVOICE (817). Comparing the size or checking the size of words excludes the third and fourth combination as possibilities. It can also serve to exclude words of different sizes on unrelated documents.

In a specific implementation, the system limits the search of other words to a predefined threshold area. A reason for the threshold is that scans often introduce an offset (as well as rotations and scale). So words of the same document often won't appear in the same place. It also helps the case where the bottom-half of an invoice (or other document) "floats." In a specific implementation, the threshold is a circle having a radius of 18 millimeters (200 pixels at 300 DPI). This helps to improve computational efficiency by reducing the number of word pairs found. It should be appreciated, however, that the algorithm can work with a circle of any radius, including an unlimited or infinite radius. A larger radius can allow for larger transformations (and hence better training or classification). The tradeoff can be computational efficiency. A large radius can be more costly.

Figure 12:
FIG. 12 shows a grid being applied to the first document example.
Figure 13:
FIG. 13 shows the grid being applied to the second document example.

In a specific implementation, the system applies a grid to the documents for searching for words for a word pair. For example, FIGS. 12-13 show a grid or matrix 1205, 1310, respectively, being applied to the documents shown in FIGS. 5-6. The documents have been partitioned, segmented, or divided into a set of tiles. The grid shown in FIGS. 12-13 has seven rows and five columns (seven by five grid) for a total of 35 tiles. It should be appreciated, however, that a grid may have any number of desired rows and any number of desired columns (e.g., five by five, eight by nine, six by eight, and so forth).

As shown in FIG. 12, there is a tile 1210 having grid coordinates [row 2, column 1]. Tile 1210 includes a first word 1215 "Peter." To search for a corresponding word in the second document, the system can access a tile having the same or adjacent grid coordinates. Note that in a specific implementation, the size of the grid is identical to the size of the radius discussed above. In this way, a word that appears two grid spaces away cannot be closer than this radius. Using a grid is an optimization. Generally, it can be desirable to limit the size of the radius in order to make effective use of the grid.

For example, as shown in FIG. 13, the system can use grid coordinates [row 2, column 1] to access a tile 1310 in order to search for a word for a word pair that corresponds to first word 1215 "Peter." Searches for a corresponding word on the second document may be limited to a tile having the same or adjacent grid coordinates. Thus, in the example shown in FIG. 13, a search for a corresponding word on the second document may be limited to a tile having grid coordinates [row 1, column 1], a tile having grid coordinates [row 1, column 2], a tile having grid coordinates [row 2, column 1], a tile having grid coordinates [row 2, column 2], a tile having grid coordinates [row 3, column 1], a tile having grid coordinates [row 3, column 2], or combinations of these. Using such a grid helps to reduce processing resources because searches for corresponding words can be limited to specific areas of the document.

In this example, tile 1310 includes a word 1315 "Peter," and a word 1320 "Canyon." A tile 1323 includes a word 1325 "Phone," and a word 1327 "Phone." These words may potentially correspond to first word 1215 "Peter" from the first document (FIG. 12). Note for the word "Phone" (1325) the system may also find the other word "Phone" (1327). This can be filtered later during the exact positioning process in the second phase of the algorithm. In an implementation, the system calculates a first factor including a Levenshtein distance between first word 1215 "Peter" from the first document and each of words 1315, 1320, 1325, and 1327 from the second document. The system calculates a second factor including a difference between an area size of first word 1215 "Peter" from the first document and each of words 1315, 1320, 1325, and 1327 from the second document. Based on the first and second factors or a score of the factors, word 1315 "Peter" from the second document is selected to be the corresponding word to word 1215 "Peter" from the first document in the word pair.

Referring now to FIG. 11, in a specific implementation, the system now having generated a set or list of word pairs (step 1115) continues on to the next phase of the algorithm which is stricter about the position. In this specific implementation, the algorithm discussed below is repeated for a range of rotations and scale. In some cases, it is sufficient to do a transformation to the bounding boxes of the set of words in one of the images and pick the transformation with the best score. This algorithm takes as input the list of pairs of words generated in the first phase (see step 1115).

In a specific implementation, the system first splits the word pairs list into "top" and "bottom" words and independently applies the same algorithm to both these sub-lists. In a specific implementation, the document image is divided in half. There is a top portion of the document and a bottom portion of the document. A first sub-list of word pairs is associated with the top portion and includes words from the top portion of the document. A second sub-list of word pairs is associated with the bottom portion and includes words from the bottom portion of the document. As discussed, in a specific implementation, the document image is divided in half or evenly so that an area of the top portion is equal to an area of the bottom portion. It should be appreciated, however, that the document may be split into any number of portions as desired including two or more unequal portions.

One reason for splitting is that on invoices and such, there is often a top and bottom that float with respect to each other. In many documents, there are often variable-sized sections in the middle of a document (such as an invoice with a list of items). So, the position of words appearing near the bottom is often not fixed with respect to the words at the top. For example, there may be two invoices that belong in the same class. A middle portion of a first invoice may include a first number of invoice items. A middle portion of a second invoice may include a second number of invoice items, different from the first number of invoice items. In a specific implementation, the algorithm splits the document into two zones including a top and bottom zone. These zones are allowed to float with respect to each other. The choice of the middle of the page can be arbitrary and a variation of the algorithm can analyze more than one split location.

In brief, in a step 1120, the system computes first location information for a word of a word pair. The first location information indicates a location of the word in the first document relative to one or more other words in the first document. In a step 1125, the system computes second location information for a corresponding word of the word pair. The second location information indicates a location of the corresponding word in the second document relative to one or more other words in the second document.

In a step 1130, the system compares the first and second location information and, in a step 1135, returns a score responsive to the comparison.

More particularly, in a specific implementation, there is an algorithm to find the words in common. The algorithm takes each word pair as a "center" and calculates the vectors to all or one or more other words on both of the document images. If the vector is approximately the same on the two images (i.e., $vect(i,j)_{img1} \approx vect(i,j)_{img2}$) then the system adds it to a list. In a specific implementation, it is approximately equal if the difference vector has a length or absolute value less than 15 pixels at 300 DPI=1.27 millimeters but this can be a tunable or user-configurable parameter.

Figure 14:
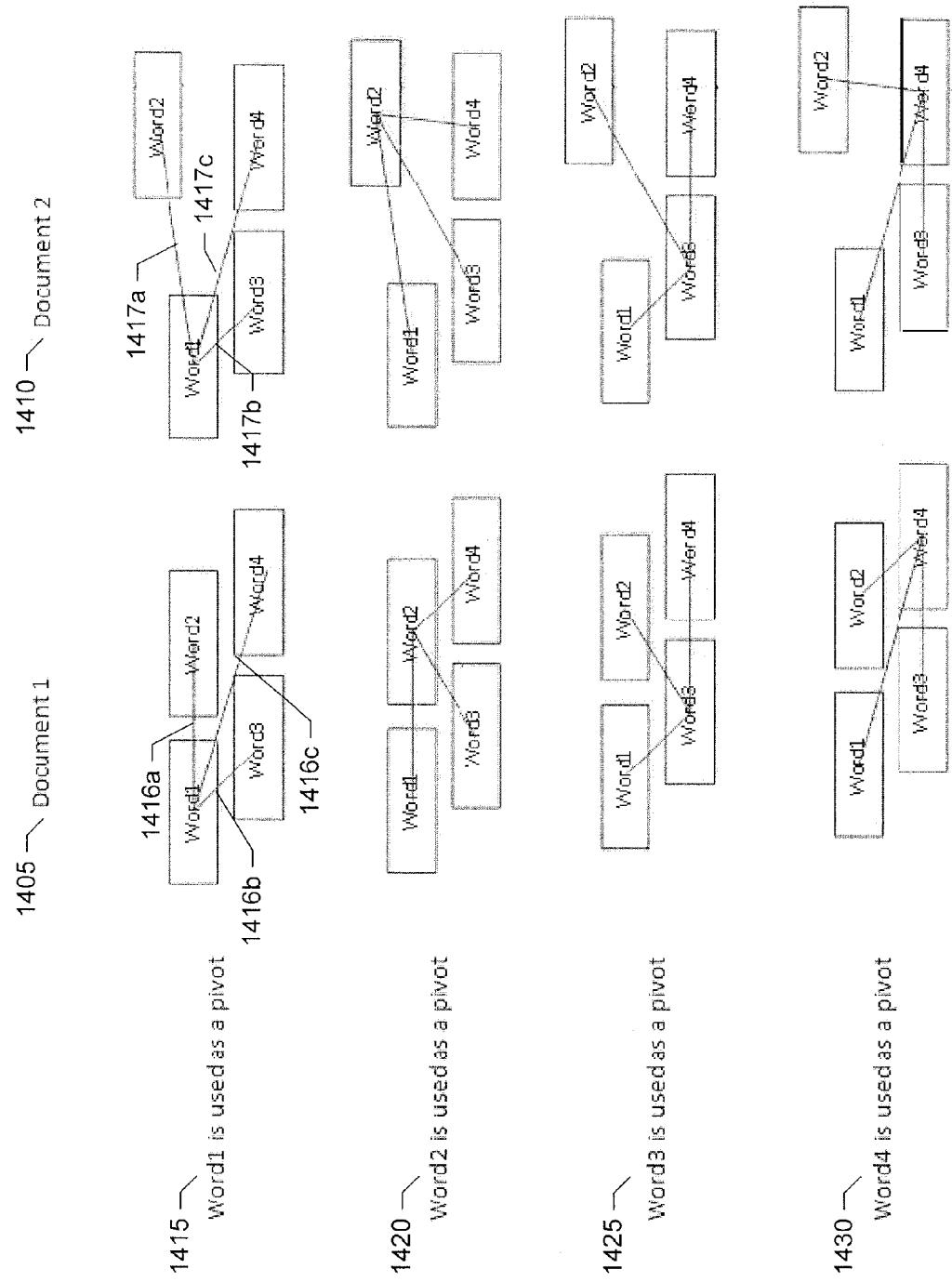
FIG. 14 shows a schematic diagram for using spatial relations of words to determine whether two documents should be in the same or different classes.

For example, FIG. 14 shows a schematic diagram for using different words in a document as pivots to calculate a location of a word in a document relative or with respect to other words in the document. As shown in FIG. 14, there is a graphical representation of positions or locations of words in first and second document 1405 and 1410, respectively. The first document includes four words word1, word2, word3, and word4. The second document includes four corresponding words word1, word2, word3, and word4.

In the first document, word1 is on a same line as word2 and is to the left of word2. Word3 and word4 are on a line below. Word 3 is offset to the right from word1. Word4 is offset to the right from word2. In the second document, word2 is on a different line from word1. Word2 is above and to the right of word1.

In a first iteration 1415 word1 is used as a pivot. The system takes word1 and calculates the vectors in each document image (vect(word1,word2), vect(word1,word3), vect(word1,word4)). For example, for the first document, a line 1416a represents a first vector calculation from word1 to word2. A line 1416b represents a second vector calculation from word1 to word3. A line 1416c represents a third vector calculation from word1 to word4. For the second document, a line 1417a represents a first corresponding vector calculation from word1 to word2. A line 1417b represents a second corresponding vector calculation from word1 to word3. A line 1417c represents a third corresponding vector calculation from word1 to word4.

Generally, a vector is a quantity that has magnitude and direction. A vector may be represented graphically as shown in FIG. 14 by a directed line segment whose length represents the magnitude and whose orientation in space represents the direction. A vector that indicates a location of a first and second word relative to each other may include a first and second set of coordinates. Each coordinate may include a first component and a second component, or an x-axis component and a y-axis component. A difference between the first components of the first and second set of coordinates may indicate a horizontal distance between the first and second words. A difference between the second components of the first and second set of coordinates may indicate a vertical distance between the first and second words.

In this example, the only combination that is different is vect(word1,word2). So, the system creates a list of word1, word3, word4. For the following iterations, the system makes the same vector calculations for word2, word3, and word4. More particularly, in a second iteration 1420 word2 is used as a pivot. In a third iteration 1425 word3 is used as a pivot. In a fourth iteration 1430 word4 is used as a pivot. This generates the lists: "word2;" "word1, word3, word4;" and "word1, word3, word4." For each list the system generates a score and selects the list with the best score. The score is based on the number of common words, their size, or both. In another specific implementation, the score may instead or additionally be based on other things such as the distribution of the words on a page (e.g., more spread out might lead to a better score). The system then combines the lists generated from the top and bottom zones and calculates the score for the combined lists. The score is compared to a threshold value or threshold score. Based on the score, the first and second documents are determined to be in the same or different class.

The scoring function takes the list of pairs of words in common between the two images. In this specific implementation, the scoring function takes the form of Score=$\alpha$CharacterCount+$\beta$CharacterArea, where $\alpha$ and $\beta$ are selected as appropriate for the particular application. In a specific implementation, the variable or parameter $\beta$ is referred to as WeightArea. The variable or parameter α is referred to as WeightCharacter. The variable CharacterCount is the sum of the number of characters in the word list. For example, the word "xyz" would count for 3 characters for each pair of words for a total of 6. The fuzzy matching, discussed above, allows the word pairs to have different character counts.

The variable CharacterArea is the sum of the area of each character in both words in the pair. Using character count instead of a word count weighs larger words more than smaller ones. The same thing is true about the area. Larger words are emphasized over smaller ones because large words are often important distinguishing features, e.g., headers or logos. In a specific implementation, α=0.4 and β=0.000875. These values were arrived at after extensive experimentation. These values were found to provide good results based on the particular documents that the system was designed to group and classify. It should be appreciated, however, that these values may vary greatly in other applications or configurations of the system. For example, the values may vary depending on the particular document types to be grouped and classified (e.g., invoices versus benefit claims). Note that in this specific implementation, the area is in 300 dpi pixels. Appropriate scaling would be done if the resolution were different.

In an implementation, if the calculated Score is larger or greater than a desired threshold (not independent of α and β), the document images will be considered to be in the same class. If the calculated score is less than the desired threshold, the document images will not be considered to be in the same class. In a specific implementation, the threshold is 210. Again, it should be appreciated that the threshold value can vary greatly depending on factors such as the particular document types to be grouped, and others.

Thus, in a specific implementation, using the specified values above for α, β, and the threshold, the test to determine whether documents are in the same class boils down to the following: 0.4 CharacterCount+0.000875 CharacterArea>210. This is approximately equivalent to about 30-40 words (this depends upon the size of words, etc.).

In a specific implementation, the score is not normalized by the number of words that appear on the document. Other approaches normalize based on the number of words on each image. The idea is that the number of common words that indicate that two images are the same will be roughly constant across different invoice and form types. If, however, the function is normalized to the number of words on the image, the system will penalize invoices that have many non-common words (e.g., 90% of the words might not be common). For example, the example invoices shown in FIGS. 5-6 are to be in the same class. Each invoice may include many listings of items that are different from the listings of items on the other invoice. Normalizing may then result in placing the two invoices in different classes because of the differences found in the listings of items.

In other implementations, the scoring function may be non-linear. There may be non-linear terms in the score. A score may further be based on the number of words on each page or in each document.

To further illustrate the textual distance feature, consider the documents shown in FIGS. 5-6. In FIG. 5, the location of word 515 "Invoice" relative to word 520 "Date" is similar to or approximately the same as the location of word 615 "Invoice" relative to word 620 "Date" in FIG. 6. This adds to the evidence that documents 505 (FIG. 5) and 605 (FIG. 6) should be in the same class.

Figure 15:
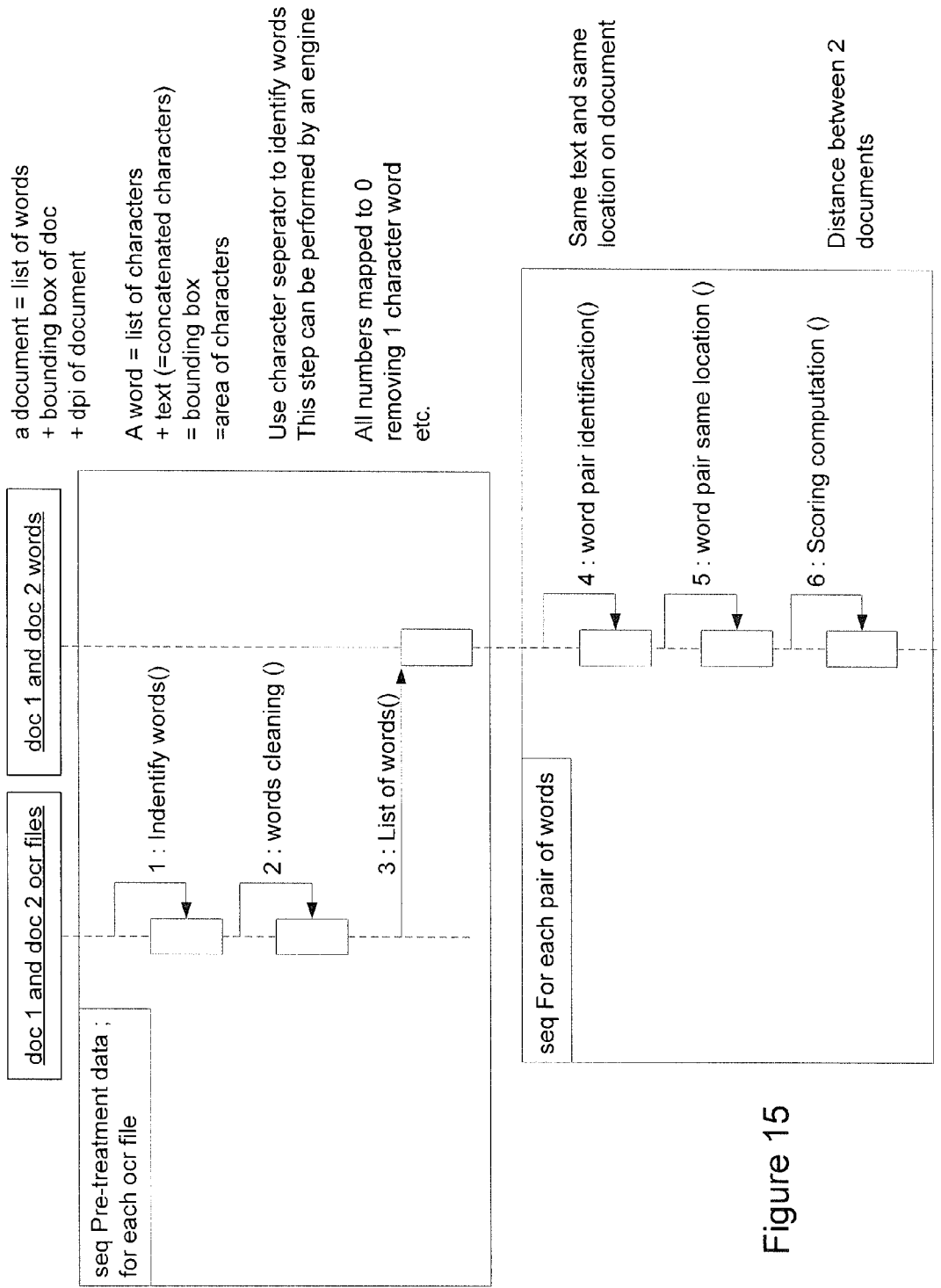
FIG. 15 shows a sequence diagram of a specific implementation of a textual distance function.
Figure 16:
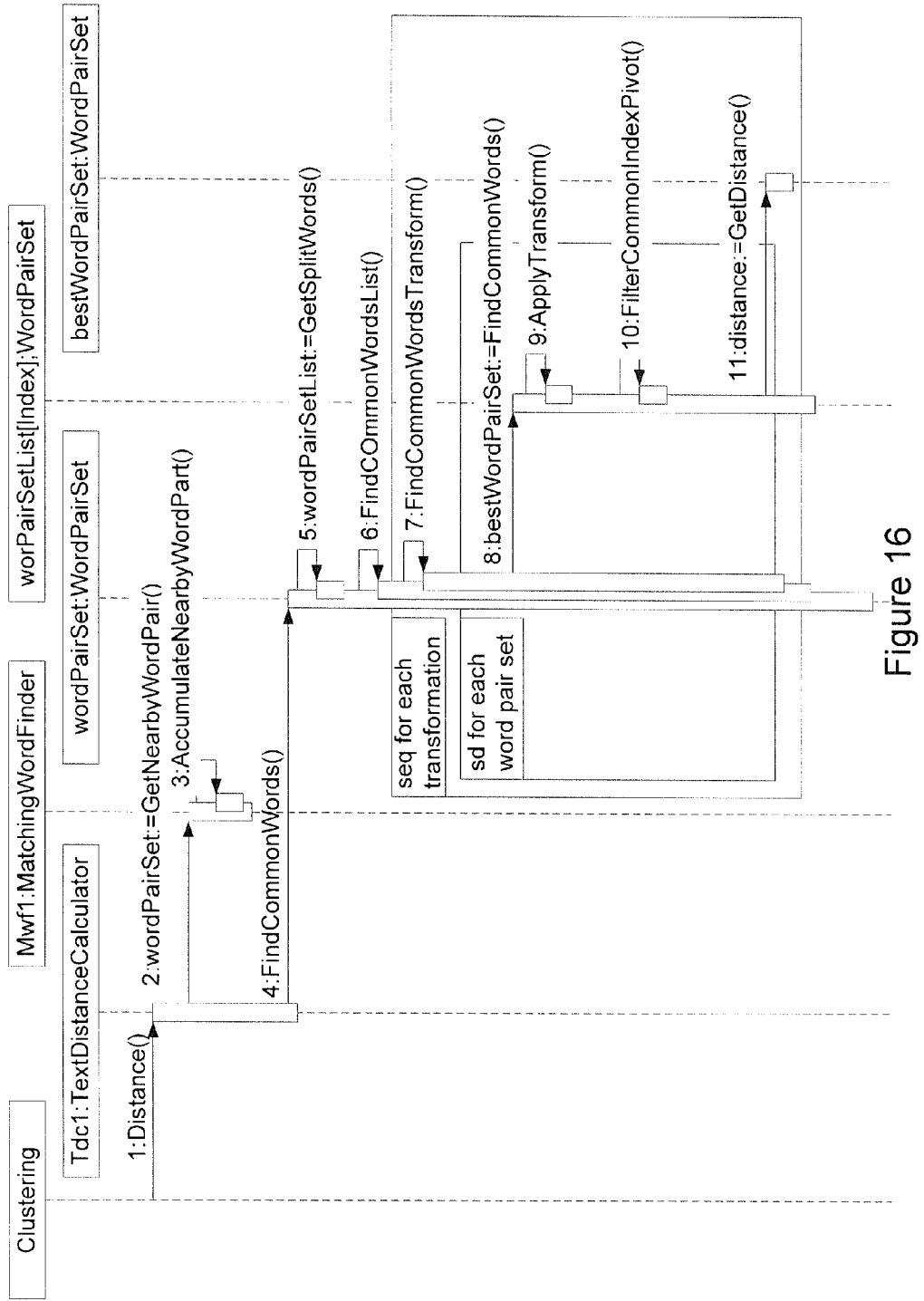
FIG. 16 shows a swimlane diagram of the distance function.

FIG. 15 shows a sequence diagram for a specific implementation of the textual distance function for a system and method for using OCR data for grouping and classifying documents. FIG. 16 shows a swimlane or process flow diagram for the sub-processes. Note that the schematics shown FIGS. 15-16 and the accompanying discussion are merely an example of one particular implementation for using the spatial relations of words to group and classify documents. In other implementations, other similar and equivalent elements, functions, object classes, and components may be used or substituted in place of what is shown.

FIGS. 15-16 and the accompanying discussion describe a specific implementation of a textual distance function that can compare documents based on textual data (e.g., OCR data) in order to determine whether two or more documents are similar or not. In this specific implementation, the textual distance function includes two variants: a "clustering" version and a "classification" version. These variants differ in the manner in which the score is generated but are generally equivalent. In the case of clustering, the system does not know a priori which words should be considered "significant," i.e., which words should be considered keywords. In classification, the system has a reference (i.e., list of keywords) in which words in that reference are considered significant.

In this specific implementation, the inputs include a document (e.g., two documents). A document includes a list of words and bounding box of the document. A word includes a list of characters, text (concatenated characters), bounding box, and area of characters. In this specific implementation, the area is the sum of width (w)×height (h) of each individual character (which may be different when there are rotated words), rather than the width (w)×height (h) of the word's bounding box. In other implementations, the area may be the width (w)×height (h) of the word's bounding box. The coordinates may be in a DPI-independent coordinate system. A document may include other information such as the location of graphical zones. In another specific implementation of the distance algorithm, the algorithm takes into account the placement, content, or both of graphical zones.

The output includes a distance value or score that may range from about 0 to 255 where a score of 0 indicates that the two documents are very close or similar and a score of 255 indicates that the two documents are not similar at all. It should be appreciated, however, that the range may be scaled differently as appropriate for the particular application and environment. In this specific implementation, there is a class referred to as TextData which represents the document, and a class referred to as TextWord which represents a word.

The Table below shows a flow for using spatial relations of words to group and classify documents.

TABLE

| Step | Description |
| --- | --- |
| (1) Read OCR Data | Output from a scanner may include an OCR file that includes a list of characters. The words may not be separated, but the list of characters may include separator characters (e.g., ' ', \t, \n). The OCR file is parsed in order to divide the list of characters into words. The code component that reads the OCR file is responsible for creating a TextData. |
| (2) Pretreat Data | The OCR data is transformed into data that facilitates computing the spatial relationships among words and provides good performance. The class TextualDistanceCalculator performs this transformation (in its constructor) and implements the distance function (it compares against another TextualDistanceCalculator object rather than directly comparing with TextData). |

TABLE-continued

| Step | Description |
| --- | --- |
| (3) Apply Distance Algorithm | The algorithm takes two documents and finds the list of word pairs (one word from each document) that obeys a set of constraints and maximizes a scoring function. |

As part of the pretreatment, the system removes a predefined set of words including words that have a single character and alters the text where the differences are not considered by the algorithm (this altering of the text is a performance enhancement—it could be just as easily done later during the comparing of text). As discussed above, in a specific implementation, the pretreatment includes (1) mapping all numbers to a predefined value, e.g., '0' and (2) rejecting words with only a single character (often this can be noise or interpreting a graphic as a letter). In other implementations, other filters may instead or additionally be used. For example, a period ('.') and a comma (',') might be confused often enough by the OCR engine such that the system may treat such characters as the same. Other prefiltering techniques to help compensate for characters that may confused by the OCR engine include mapping upper case "I," lower case "L," and the number "1," to the same predefined character. Mapping the number "0" and upper case "O" to the same predefined character.

It is desirable to keep track that the word has changed. The fact that a word has been modified is used to lower the weight of a word during the keyword learning step. It can also be useful to use this in the distance function itself.

As discussed above, one reason for mapping all numbers to a predefined value, e.g., '0' is that variable number fields may be in the same place but with different numerical values. So, the system treats "123.45" and "567.89" as equivalent. The Levenhstein distance helps to make comparisons with variable number of digits. Application of the Levenhstein distance may result in a first word including a first number of digits being matched to a corresponding second word including a second number of digits, different from the first number of digits. For example, the text "1234.56" may be made equivalent to "987.65." In other implementations, confidence values of characters, their alternates, or both may instead or additionally be used to match or identify a word and a corresponding word.

In a specific implementation, a pretreatment step, as described below, includes creating a 2-dimensional array of lists of words (stored in the MatchingWordFinder class).

As discussed, the distance algorithm can take two documents and find the list of word pairs (one word from each document) that obeys a set of constraints and maximizes a scoring function. In this specific implementation, the constraints on this list of word pairs include a first constraint that a word must be the "same" or equivalent on both document images (see further discussion below). A second constraint includes that the set of words from the first image must be close to the same relative position on the two images. Relative position provides that after a transformation is applied to the coordinates of the set of words on an image (the transformation allows for translation, scaling and rotation) that the boxes are in the same position (e.g., less than 15 pixels at 300 dpi) in the two documents. The algorithm divides the words into top and bottom zones with independent translations but not independent scale and rotation. The transformation is the same for each word. The range of transformations to test for is a set of parameters that can be tuned, configured, or adjusted as desired. Generally, the larger the range, the longer the algorithm takes but the more accurate it will be.

Words may be the "same" or equivalent on two images if the distance between the centers of each word is less than or below a threshold value (e.g., <RectDistThreshold=200 pixels@300 dpi). This parameter helps to limit the number of choices considered in order to conserve computing resources and help ensure rapid code execution. It should be appreciated that the parameter may be set to infinite in certain applications.

Words may be the "same" or equivalent on two images if the area is about the same. In a specific implementation, a difference between the areas must be less than 50 percent. That is, a parameter AreaTolerance=0.5—so the areas for two words to be equivalent cannot be more than 50 percent different. It should be appreciated that the parameter can be configurable and can be set to any threshold value.

Words may be the "same" or equivalent on two images if the text is about the same based on a value of a string metric (e.g., Levenhstein distance<LevensteinThreshold).

In a specific implementation, the scoring function for the clustering distance is:

Score=Sum for all matching words
(WordArea*WeightArea+
NumberCharacters*WeightCharacter)

As discussed above WeightArea and WeightCharacter may be represented by the variables or parameters $\beta$ and $\alpha$, respectively.

From this the system obtains a "distance" by calculating:

Distance=TextDistanceParameters.BaseScore−Score
(if <0, distance=0, if >255, distance=255)

Through experimentation, this scoring was determined to provide good results. In an implementation, the distance function looks for an absolute number of words in common not a relative number. In another implementation, the distance function may instead or additionally look for a relative number.

As discussed, the use of the area in the score provides that words in a larger font size are weighted more than those in a smaller size. One reason is because applicants have found that for certain document types large words tend to be things such as logos that are likely more significant than smaller words. This is not, however, necessarily always the case. For example, depending upon the document types to be classified, words in a larger font may not be weighted more than those in a smaller size. For example, words in a larger font may be weighted the same as those in the smaller size. Words in a larger font may be weighted less than those in the smaller size.

In other specific implementations, the function includes a normalization technique to help ensure that the distance between two blank documents is the same. The normalization technique, however, is not a strict percentage (e.g., a distance of 128 for 50 percent of words in common). One advantage of not normalizing using a strict percentage is because on some documents of interest, there may be a lot of words that can be irrelevant (e.g., rows in an invoice). It can be desirable to be insensitive to this sort of variation. Further, finding, for example, 50 words in common may indicate the same document type. For example, if the system finds 50 of 150 words the distance may be close to 0. But, if the system finds 1 of 3, it may not be very significant.

In a specific implementation, the algorithm is further adapted for scoring for classification distance. In this specific implementation, the list of template keywords is the same structure as the list of words. One difference, however, may be the scoring function. The scoring function may be different because the system knows that the list of keywords should be present (as discussed, when comparing two unknown images the system may not have information about which words should be present but when the system has the keywords a word being absent may be significant). See FIG. 17 and accompanying description for a more detailed discussion of document templates.

The algorithm may be implemented using two main phases. In a first phase, the algorithm finds a list of nearby word pairs that are the same or equivalent words in the two documents. In a second phase the algorithm refines the list to find the list of words that are in about the same position (after a transformation) in the two documents.

For finding nearby words, the first part of the algorithm is implemented in MatchingWordFinder. The constructor of MatchingWordFinder takes a list of words and breaks them up into a grid of lists of words organized by the position of each word. Each element of the grid represents an area on the image of RectDistThreshold×RectDistThreshold.

For example, position 3, 5 has a list of words whose centers are between 3*RectDistThreshold<=x<(3+1)*RectDistThreshold and 5*RectDistThreshold<=y<(5+1)*RectDistThreshold. This grid is created once per document and is reused for each call to the distance function.

The routine GetNearbyWordPairs takes two MatchingWordFinders and creates a list of WordPairs (WordPairSet) for the words that are the same in each document. Because the system looks for words whose centers have a distance<RectDistThreshold, the search can be limited to the neighboring grid areas. See code sample below:

```
WordPairSet wps = new WordPairSet( )
    For each Image1.GridElement
        For each Image2.GridElement that is within 1 element
        (x±1, y±1) of Image1.GridElement
            AccumulateNearbyWordPairs(wps,
    Image1.GridElement.WordList, Image2.GridElement.WordList)
```

The AccumulateNearbyWordPairs iterates though every combination in the two lists. A word might appear multiple times. For example, the word "x" might occur on the second image in several places. In this case, the system adds one pair for each occurrence. Duplicates are filtered out in the second phase of the algorithm because at this point the system does not know which "x" is going to be in the same relative position.

With the set of nearby word pairs, the algorithm moves to the second phase for finding words in the same relative position. The system looks for the list of words that maximize a scoring function that are on the two images and are in the same place on both images.

Specifically, the image is divided into "top" and "bottom" words. As discussed above, on some documents such as invoices, the top and bottom portions vary with respect to each other—on forms or other document types splitting the image has been found unlikely to cause a loss of accuracy.

Then, for a set of transformation (using variations of scale and rotation), the system finds the set of words in the same place (after the transformation is applied). The transformation helps to ensure that word coordinates or locations can be compared.

For each Transformation t
    FindCommonWords(t)
As discussed in the description accompanying FIG. 11, to find the common words, the system takes each word in the word set and uses this as a pivot. With this pivot word, the system takes each other pair of words and calculates the vectors:
img1.wpivot.bounds.Center–img1.w.bounds.Center and
img2.wpivot.transformedBounds.Center–img2.w.transformedBounds.Center If these vectors are close (e.g., the difference between these vectors has a length less than WordCloseness=15 pixels@300 dpi), then they are determined to be in the same position and added to the list.

In a specific implementation, there is an optimization technique that applies the vector calculation to at most a subset of words. Applicants have discovered that applying the vector calculation to every third word can improve performance without degrading the results. The system applies the vector calculation for both the "top" and "bottom" lists and makes one list of top+bottom.

A vector calculation is made for each pivot and for each list a score is calculated. The system identifies the "best" list, i.e., the list that maximizes the score. In the function, this list may be returned so that it can be used in the algorithm for learning keywords.

Figure 17:
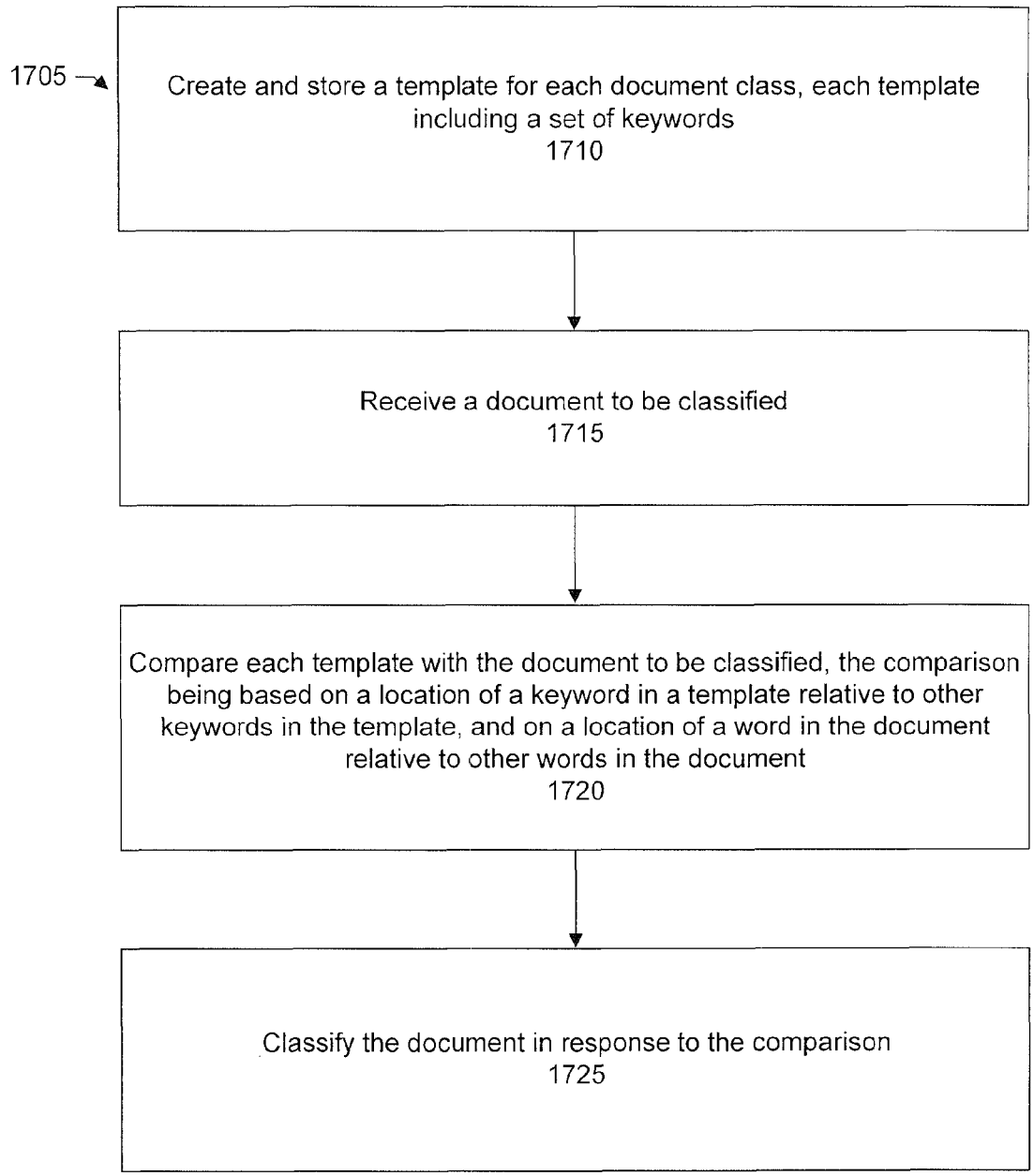
FIG. 17 shows an overall flow for creating document templates and classifying a document using the document templates.

FIG. 17 shows a flow 1705 for creating document templates and classifying documents based on the document templates. In brief, in a step 1710, the system creates and stores a template for each document class (see FIGS. 9-11 and accompanying description for a discussion of creating document classes). Each template includes a set or list of keywords. The templates may be stored in a template database. In a step 1715, the system receives as input a document to be classified. For example, the document may be received from a scanner or other OCR datastream. In a step 1720, the system compares each template with the document to be classified. In a specific implementation, each template in the set of templates is tried. The comparison is based on the spatial relations of the keywords in a template and the words in the document to be classified. More particularly, the comparison is based on a location of a keyword in a template relative to other keywords in the template, and on a location of a word in the document relative to other words in the document. In a step 1725, the system classifies the document in response to the comparison.

In a specific implementation, a document template associated with a document class includes a set of keywords and location information indicating a location of a keyword in the template relative to one or more other keywords in the template. Upon creating the set of document classes based on grouping the set of training documents, the system can create a document template to be associated with each of the document classes. In other words, once there is a set of document images that are of the same class, system determines a set of words that appear in all (or at least most) of the documents. The set of words may be referred to as the keywords of a template. It is also possible for a user to define this list of keywords. The list of keywords may include words provided by the system (based on the system's analysis of the documents), words provided by a user, or both.

In this specific implementation, a keyword learning algorithm takes the collection of document images in a class and outputs a set of words in common. The algorithm starts by getting or obtaining the common set of words between each pair of documents. This can be accomplished using the same algorithms in the distance function discussed above.

The system then creates a matrix of words in each document (e.g., docCount X words). For each pair of words in the common words set of each pair of documents, the system executes the following procedure (for documents i, j):

1. If the word x already exists in the list either document add in the new pair (note that one of these words must already be there)
   a. If (not null words[x][i])
   words[x][i]=wordPair.word(doc i)
   b. If (not null words[x][j])
   words[x][j]=wordPair.word(doc j)
2. If it does not exist, then add the pair to the list
   a. words[x][i]=wordPair.word(doc i)
   b. words[x][j]=wordPair.word(doc j)

This generates a list giving the information, for example, "word X appears in document A, B, C and D," "word Y appears in documents A and D," and so forth. The list may include a word, and a number of documents that the word has been found in, an identification of the documents that the word has been found in, or both.

In a specific implementation, the system then sorts this list by another scoring function (which is a different scoring function from the distance function) that takes into account the number of documents a word is found in, the size of the word, and whether or not it is an exact match.

A selection is made of the top N words that have a score at least equal to a threshold. The value of N may range from about 30-40. Generally, more words may provide more accurate results, but may increase the processing time when using the words in classification. So, depending on the specific application of the system, the desired accuracy, and available computing resources, the value of N may be less than 30 or greater than 40.

For each word, the system then transforms its box into a common coordinate system. The first document image in the set may be identified as the "master" document image providing the coordinate system. This choice is arbitrary.

In this specific implementation, the bounding box for a word is:
Average(Transform(master, i)(word.Bounds(doc i))

The word text to be used is the word which occurs most often or most frequently. As discussed, the text might be slightly different in each word because of the fuzzy word match. The output includes a set of words, i.e., keywords that are common across a set of document images in a class.

In a specific implementation, a document template is created that includes the keywords. Upon receipt of a document to be classified, the document is compared against the template and is classified in response to the comparison (see FIG. 17 and accompanying discussion above).

In a specific implementation, a template includes a set of keywords and first location information that indicates a location of a keyword in a template relative to one or more other keywords in the template. The system receives a document to be classified.

The system selects a template. In this specific implementation, selecting a template is based on a scoring function for classification between a document image and a set of keywords. Generally, the classification scoring function includes more or additional information than the training scoring function. As discussed above, one reason is because through the keyword learning algorithm, there is a list of words, i.e., keywords that ought to be on a given document image if it is in the given class. This is in contrast to the training function which is looking for similarities between two document images with no a priori knowledge of the contents of the two images. This can change the underlying form of the function.

It should be appreciated that due to training errors, OCR errors, and other problems with the document image, there may not be 100 percent of the keywords of a template found in the received document. For example, the system may find that an address that is the same for all the training samples but actually changes in a real situation.

The scoring function can use the same word-finding algorithm as in the training distance function. A score is calculated that indicates the percentage of words found. If there are a sufficient number of words found, the document should be able to be classified. The percentage of words found can be compared to a threshold value. In a specific implementation, the threshold value is about 65 percent, but can vary depending upon the application and desired results. For example, the value may be greater or less than 65 percent. See code sample below:

const int maxWords=30; \\ this can be changed
commonWords=GetCommonWords(keywords, image);
countDoc min(keywords.Count, maxWords);
countRef min(commonWords.Count, maxWords);
score=commonWords.Count/keywords.Count;
boolean is Classified=(score>threshold);

To classify a document using a template, the system generates a set of word pairs. Each word pair includes a keyword from the set of keywords of the selected template and a corresponding word from the document to be classified—see step 1115 (FIG. 11) and accompanying description of generating word pairs. The system computes second location information for a corresponding word of a word pair. The computed second location information indicates a location of the corresponding word of the word pair in the document to be classified relative to one or more other words in the document—see steps 1120-1125 (FIG. 11) and accompanying description of computing word location information.

The system compares the second location information against the first location information and returns a score responsive to the comparison that can be used to determine whether or not the received document should be classified in the document class associated with the template. Classifying the document in the document class may include tagging the document with a tag or other metadata information that indicates the document class.

This application describes aspects of the invention in connection with the spatial relationships of words. Principles of the invention, however, are also applicable to graphics including pictures, photographs, graphical images, charts (e.g., pie charts, bar charts, or graphs), or graphical symbols. In other words, the search for common words can be extended to graphics. A technique for grouping and classifying documents with graphics may include finding zones of graphics and a function to determine whether graphics are the same or equivalent. If the same graphic appears in the same position it adds to a confidence rating indicating that it is the same document. This can be mixed with the textual matching.

In a specific implementation, the algorithm is adapted to words (e.g., a group of two or more characters) rather than individual characters. In other implementations, the algorithm may be adapted for individual characters, groups of words (e.g., sentences, phrases, paragraphs), a document line, or combinations of these.

In a specific implementation, the existing algorithm when comparing to see if two words are the "same" or equivalent does not use character confidences or alternate choices—e.g., number "0" versus capital letter "O"—which may be provided by the OCR engines. In another specific implementation, comparisons include the confidence ratings. Using confidences can enhance the comparisons function. Further, instead of a Boolean decision on sameness or equivalency, there can be a confidence value used in the scoring function.

There can be other separate uses for the underlying textual/position matching algorithm. For example, in another specific implementation, an anchor is generated which includes a collection of words around a field (e.g., the words "total," "tax," and "subtotal" may appear in the same positions consistently and if two of the three are found one may be fairly sure to have found the right place). Using a collection of words (e.g., two or more words) as an anchor offers benefits over using a single unique text or graphic to locate a field because there can be problems with noise or markings (such as handwriting) on a document image.

Using the spatial relations of words to determine whether two documents belong in the same document class has advantages over graphical-based distance functions for training and classification. Typically, graphical-based distance functions "blur" an image or use low-resolution reductions in order to ignore variations such as different words, and so forth. This technique may be adequate for document images that do not change much from one document to another of the same class—for example, in forms where the majority of the image comes from the underlying form or where the graphics are particularly bold (e.g., invoices that have a lot of black pixels in the underling template).

However, when the document images have fewer graphics and the pages are generally lighter, small variations such as stamps 550 (FIG. 5) tend to greatly skew the distance function. For example, documents 505 and 605 may be placed into different classes by such a distance function even though to a human eye they may be related. The stamps and the noise in the image cause this graphical distance to become large. Further, differences in the content of invoices (with varying number of lines, invoice items, or both) can confuse other classification algorithms. In the case of semi-structured documents such as invoices, graphical differences within the same type of documents can be large, especially when an invoice has a variable sized table. This results in substantially suboptimum grouping and low classification rates.

The distance function as discussed in this application overcomes these deficiencies and can classify the documents correctly. Further, the techniques described in this application can take into account minor transformations such as small rotations and scaling. For example, scanned images are often rotated because the physical page perhaps was not perfectly placed or aligned on the scanner and notions such as dots per inch ("DPI") may only be approximate and not perfectly consistent from scanner to scanner. In an implementation, the system is completely scale and rotation independent. A technique as discussed in this application allows for much higher classification rates and lowers document management and processing costs.

In a specific implementation, a technique for classifying documents is based on position and text. A "template" includes N boxes with text (character or word). A character may provide good results, but may increase the processing time. There can be graphic boxes as well. To classify a target document, an OCR is performed on the target to match the N boxes. The template can be shifted around until a desirable match is achieved. This can be accomplished by using boxes+ text. OCRd text not part of the classification may be ignored.

In this specific implementation, for clustering, the system takes a set of images. One at a time, the system checks against all the previous images. If a match is found, the document images are placed in the same bucket. An iterative process using progressively higher thresholds for matching may be used for refining. In a specific implementation, the system counts the number of matched characters and ignores mismatched (assuming any mismatch may be due to variable text). To be matching, the same, or equivalent, the relative offsets and sizes of text boxes should be the same or equivalent. That is, if there is a word "X" that is (x, y) away from a word "Y" to match another image the same pair of letters must be the same relative position and the letters must be of the same size. There can be a small margin for variations (e.g., at most about a tenth of a character in size).

Once a collection of images have been obtained that seem to be of the same collection (using "loose" criteria), the system obtains the set of text/boxes that are common to all (or at least most). Some recognition errors may be tolerated but the system can be fairly strict, especially when creating the clusters, as it is not necessary to have the complete set of words in common.

The algorithm may be biased to weigh larger text more heavily because larger text can be typical of logos. A rotational invariance may be obtained by using distances rather than looking just at delta-x, delta-y. A requirement may be that at least 3 "keywords" are obtained. An OCR engine may provide a larger bounding box for a rotated character which the system can account for. At the end of the clustering, there is a collection of templates. Each template includes a set of N keywords including of text positions and values (e.g., word "x" at (123, 456) of size (20, 20)).

At classification-time, the system determines how many of these match and takes the largest number of matches (or highest percentage). The classification algorithm may be similar to the algorithm that makes the clusters. In an implementation, there is an additional variable for number of lines. A single degree of freedom may be assumed. Some "keywords" could float by the number of lines in the OCR results.

In a specific implementation, as discussed above, a location or spatial location of a word in a document is with respect to the centers of other words in the document (see FIG. 14). That is, a center of a word is used as a reference point. In other specific implementations, a reference point may not be at the center of a word. For example, the reference point may be at the beginning of the word, the end of the word, or at any arbitrary location within the document (e.g., upper left hand corner, upper right hand corner, lower left hand corner, or lower right hand corner).

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment.

What is claimed is:

1. A system for creating classes for classifying digitized documents, the system comprising:
   a processor-based document management system comprising at least one processor coupled to a memory executed on a computer system and configured to:
   generate a plurality of word pairs, each word pair comprising a word from a first digitized document, and a corresponding word from a second digitized document;
   compute for each word pair first location information for the word that indicates a location of the word in the first digitized document relative to other words in the first digitized document;

compute for each word pair second location information for the corresponding word that indicates a location of the corresponding word in the second digitized document relative to other words in the second digitized document;

compare the first and second location information; and create one or more classes responsive to the comparison to classify digitized documents similar to the first digitized document, and to classify digitized documents similar to the second digitized document.

2. The system of claim 1 wherein the processor-based document management system is further configured to:

if the comparison indicates locations of words in the first digitized document are the same as locations of corresponding words in the second digitized document, determine that the first and second digitized documents should be in a same class; and upon the determination that the first and second digitized documents should be in the same class, create a class to classify documents similar to the first and second digitized documents.

3. The system of claim 1 wherein the processor-based document management system is further configured to:

if the comparison indicates the locations of words in the first digitized document are different from the locations of the corresponding words in the second digitized document, determine that the first and second digitized documents should be in different classes; and upon the determination that the first and second digitized documents should be in different classes, create a first class to classify digitized documents similar to the first digitized document, and create a second class, different from the first class, to classify digitized documents similar to the second digitized document.

4. The system of claim 1 wherein the first location information comprises top location information, and bottom location information, the top location information is associated with a top portion of the first digitized document, and comprises a location of a word in the top portion of the first digitized document relative to other words in the top portion, and the bottom location information is associated with a bottom portion of the first digitized document and comprises a location of a word in the bottom portion of the first digitized document relative to other words in the bottom portion.

5. The system of claim 1 wherein the processor-based document management system is further configured to:

calculate a first vector from the word in the first digitized document to a first other word in the first digitized document, the first vector thereby indicating a location of the word relative to the first other word; and calculate a second vector from the word in the first digitized document to a second other word in the first digitized document, the second vector thereby indicating a location of the word relative to the second other word.

6. The system of claim 1 wherein the processor-based document management system is further configured to:

calculate a Levenshtein distance between a word from the first digitized document and a word from the second digitized document;

determine that the Levenshtein distance is below a threshold value; and based on the determination, identify the word from the first digitized document as being a word for a word pair, and identify the word from the second digitized document as being a corresponding word for the word pair.

7. The system of claim 1 wherein the processor-based document management system is further configured to:

calculate a first value that indicates an area occupied by a word in the first digitized document;

calculate a second value that indicates an area occupied by a word in the second digitized document;

determine that a difference between the first and second values is below a threshold value; and based on the determination, identify the word in the first digitized document as being a word for a word pair, and identifying the word in the second digitized document as being a corresponding word for the word pair.

8. The system of claim 1 wherein the processor-based document management system is further configured to:

map each numerical digit of a first number in the first digitized document to a predefined value to alter the first number to a first altered number; and map each numerical digit of a second number, different from the first number, in the second digitized document to the predefined value to alter the second number to a second altered, number, the same as the first altered number, thereby permitting the first altered number to be considered as a word for a word pair, and the second altered number to be considered as a corresponding word for the word pair.

9. A method implemented by a computer comprising at least one processor for creating classes for classifying digitized documents comprising:

generating a plurality of word pairs, each word pair comprising a word from a first digitized document, and a corresponding word from a second digitized document;

computing for each word pair first location information for the word that indicates a location of the word in the first digitized document relative to other words in the first digitized document;

computing for each word pair second location information for the corresponding word that indicates a location of the corresponding word in the second digitized document relative to other words in the second digitized document;

comparing the first and second location information; and creating one or more classes responsive to the comparison to classify digitized documents similar to the first digitized document, and to classify digitized documents similar to the second digitized document.

10. The method of claim 9 comprising:

if the comparison indicates locations of words in the first digitized document are the same as locations of corresponding words in the second digitized document, determining that the first and second digitized documents should be in a same class; and upon the determination that the first and second digitized documents should be in the same class, creating a class to classify documents similar to the first and second digitized documents.

11. The method of claim 9 comprising:

if the comparison indicates the locations of words in the first digitized document are different from the locations of the corresponding words in the second digitized document, determining that the first and second digitized documents should be in different classes; and upon the determination that the first and second digitized documents should be in different classes, creating a first class to classify digitized documents similar to the first digitized document, and creating a second class, different from the first class, to classify digitized documents similar to the second digitized document.

12. The method of claim 9 wherein the first location information comprises top location information, and bottom location information, the top location information is associated with a top portion of the first digitized document, and comprises a location of a word in the top portion of the first digitized document relative to other words in the top portion, and the bottom location information is associated with a bottom portion of the first digitized document and comprises a location of a word in the bottom portion of the first digitized document relative to other words in the bottom portion.

13. The method of claim 9 wherein the computing first location information for the word that indicates a location of the word in the first digitized document relative to other words in the first digitized document comprises:

calculating a first vector from the word in the first digitized document to a first other word in the first digitized document, the first vector thereby indicating a location of the word relative to the first other word; and calculating a second vector from the word in the first digitized document to a second other word in the first digitized document, the second vector thereby indicating a location of the word relative to the second other word.

14. The method of claim 9 wherein the generating a plurality of word pairs comprises:

calculating a Levenshtein distance between a word from the first digitized document and a word from the second digitized document;

determining that the Levenshtein distance is below a threshold value; and based on the determination, identifying the word from the first digitized document as being a word for a word pair, and identifying the word from the second digitized document as being a corresponding word for the word pair.

15. The method of claim 9 wherein the generating a plurality of word pairs comprises:

calculating a first value that indicates an area occupied by a word in the first digitized document;

calculating a second value that indicates an area occupied by a word in the second digitized document;

determining that a difference between the first and second values is below a threshold value; and based on the determination, identifying the word in the first digitized document as being a word for a word pair, and identifying the word in the second digitized document as being a corresponding word for the word pair.

16. The method of claim 9 wherein the generating a plurality of word pairs comprises:

mapping each numerical digit of a first number in the first digitized document to a predefined value to alter the first number to a first altered number; and mapping each numerical digit of a second number, different from the first number, in the second digitized document to the predefined value to alter the second number to a second altered number, the same as the first altered number, thereby permitting the first altered number to be considered as a word for a word pair, and the second altered number to be considered as a corresponding word for the word pair.

17. A computer program product, comprising a non-transitory computer-readable medium having a computer-readable program code embodied therein, the computer-readable program code adapted to be executed by one or more processors to implement a method comprising:

generating a plurality of word pairs, each word pair comprising a word from a first digitized document, and a corresponding word from a second digitized document;

computing for each word pair first location information for the word that indicates a location of the word in the first digitized document relative to other words in the first digitized document;

computing for each word pair second location information for the corresponding word that indicates a location of the corresponding word in the second digitized document relative to other words in the second digitized document;

comparing the first and second location information; and creating one or more classes responsive to the comparison to classify digitized documents similar to the first digitized document, and to classify digitized documents similar to the second digitized document.

18. The computer program product of claim 17 wherein the method comprises:

if the comparison indicates locations of words in the first digitized document are the same as locations of corresponding words in the second digitized document, determining that the first and second digitized documents should be in a same class; and upon the determination that the first and second digitized documents should be in the same class, creating a class to classify documents similar to the first and second digitized documents.

19. The computer program product of claim 17 wherein the method comprises:

if the comparison indicates the locations of words in the first digitized document are different from the locations of the corresponding words in the second digitized document, determining that the first and second digitized documents should be in different classes; and upon the determination that the first and second digitized documents should be in different classes, creating a first class to classify digitized documents similar to the first digitized document, and creating a second class, different from the first class, to classify digitized documents similar to the second digitized document.

20. The computer program product of claim 17 wherein the first location information comprises top location information, and bottom location information, the top location information is associated with a top portion of the first digitized document, and comprises a location of a word in the top portion of the first digitized document relative to other words in the top portion, and the bottom location information is associated with a bottom portion of the first digitized document and comprises a location of a word in the bottom portion of the first digitized document relative to other words in the bottom portion.

* * * * *